US011433000B2

(12) United States Patent
Arias et al.

(10) Patent No.: US 11,433,000 B2
(45) Date of Patent: Sep. 6, 2022

(54) SYSTEM TO MANAGE THE SAFE DISTRIBUTION OF MEDICINES AND TO CONTROL HEALTHCARE VARIABLES

(71) Applicants: Rodrigo Arias, Montevideo (UY); Roberto Perez, Montevideo (UY)

(72) Inventors: Rodrigo Arias, Montevideo (UY); Roberto Perez, Montevideo (UY)

(*) Notice: Subject to any disclaimer, the term of this patent is extended or adjusted under 35 U.S.C. 154(b) by 0 days.

(21) Appl. No.: 17/046,006

(22) PCT Filed: Oct. 5, 2018

(86) PCT No.: PCT/IB2018/057753
§ 371 (c)(1),
(2) Date: Oct. 8, 2020

(87) PCT Pub. No.: WO2019/197891
PCT Pub. Date: Oct. 17, 2019

(65) Prior Publication Data
US 2021/0022962 A1 Jan. 28, 2021

(30) Foreign Application Priority Data

Apr. 12, 2018 (UY) .......................................... 37675

(51) Int. Cl.
*A61J 7/00* (2006.01)
*A61J 7/04* (2006.01)
(Continued)

(52) U.S. Cl.
CPC ........... *A61J 7/0084* (2013.01); *A61J 7/0436* (2015.05); *A61J 7/0445* (2015.05); *A61J 7/0481* (2013.01);
(Continued)

(58) Field of Classification Search
CPC ...... A61J 7/0084; A61J 7/0436; A61J 7/0445; A61J 7/0481; A61J 2200/30; A61J 2200/70; A61J 2205/60; G16H 40/67; G16H 20/13
See application file for complete search history.

(56) References Cited

U.S. PATENT DOCUMENTS 4,572,403 A * 2/1986 Benaroya .................. A61J 7/04
221/15
6,021,918 A * 2/2000 Dumont ................ A61J 7/0481
221/2

(Continued)

FOREIGN PATENT DOCUMENTS

CN 107822891 A 3/2018
WO 2002017850 A1 3/2002
(Continued)

*Primary Examiner* — Michael Collins
(74) *Attorney, Agent, or Firm* — Hoglund & Pamias, PSC; Roberto J Rios

(57) ABSTRACT

The present invention deals with an intelligent device, connected to the internet, providing for the safe storage and delivery of medicines in an automatic and controlled manner. In addition, it allows for health checks to be made on the patient using data obtained through peripheral devices, which are not the subject of this invention. Thus it is an electromechanical device together with the necessary software both in the device and in external applications, to improve compliance with pharmacological treatments for patients, also generating reliable information and enabling continuous monitoring of the patient by the responsible person.

15 Claims, 5 Drawing Sheets

(51) Int. Cl.
*G16H 20/13* (2018.01)
*G16H 40/67* (2018.01)

(52) U.S. Cl.
CPC .............. *G16H 20/13* (2018.01); *G16H 40/67* (2018.01); *A61J 2200/30* (2013.01); *A61J 2200/70* (2013.01); *A61J 2205/60* (2013.01)

(56) References Cited

U.S. PATENT DOCUMENTS

| | | | |
|---|---|---|---|
| 7,269,476 B2 | 9/2007 | Ratnakar | |
| 8,670,865 B2* | 3/2014 | Coe | G07F 9/026 700/243 |
| 9,579,264 B1* | 2/2017 | Litton | G07F 13/025 |
| 9,889,069 B1* | 2/2018 | Coe | G06F 3/041 |
| 10,335,349 B2* | 7/2019 | Roslyakov | A61J 7/0076 |
| 10,555,874 B2* | 2/2020 | Feng | G06F 3/01 |
| 10,821,054 B1* | 11/2020 | Howton | A61J 7/0481 |
| 10,993,881 B1* | 5/2021 | Karpman | G16H 20/13 |
| 11,147,742 B1* | 10/2021 | Omokhodion | A61J 7/0445 |
| 2006/0124655 A1 | 6/2006 | Ratnakar | |
| 2006/0124658 A1* | 6/2006 | Coe | A61J 7/04 221/121 |
| 2012/0316405 A1 | 12/2012 | Taylor | |
| 2014/0131378 A1* | 5/2014 | Shih | A61J 7/04 221/211 |
| 2021/0100722 A1* | 4/2021 | Hines | A61J 7/0436 |

FOREIGN PATENT DOCUMENTS

| | | |
|---|---|---|
| WO | 2008044990 A1 | 4/2008 |
| WO | 2013120029 A1 | 8/2013 |
| WO | 2016141102 A1 | 9/2016 |

* cited by examiner

SYSTEM TO MANAGE THE SAFE DISTRIBUTION OF MEDICINES AND TO CONTROL HEALTHCARE VARIABLES

TECHNICAL AREA

The present invention refers to the area of medical products, particularly to devices capable of managing, storing and distributing medicines.

Definitions

In order to have a better understanding of the present invention a series of definitions are included:

Pillbox: a device with sections whose main function is to store and deliver medicines in a controlled manner.

Peripheral Devices: sensors that connect to the pillbox wirelessly to obtain medical data on the patients' health, generate warnings to patients/users/responsible persons, see their location and enable two-way communication between patient/user/responsible persons.

Expansion modules: optional modules that can be added to the device to add functionalities to the system (such as a module for indoor environmental control).

Patient: a person who uses the system to follow a pharmacological treatment programme, to access the health system in some way or to remotely check their health data.

User: a person who uses the system through the application of a smartphone, web or a computer programme to control compliance with a treatment programme by one or more patients, upload treatment programmes, as well as monitor the health measurements of their assigned patients. It can be enabled or not by the responsible person in order to perform the functions explained above. A user can also be a patient.

Responsible Person: a person who has total control over the system (pillbox, peripherals devices, etc.), who in turn can also delegate permissions to other users to carry out actions on the system. The responsible person can, in turn, be a patient and user.

Application (APP): A multiplatform software that allows one to manage all the functions of the pillbox remotely, receive and consult biometric measurements of the patients, view the history of medications administered to patients, see treatment and environmental parameters as well as the operation of the pillbox. The software can be used in a variety of platforms such as: Android, IOS, MacOS, Windows, Linux, FireFoxOS, Symbian, etc.

BACKGROUND

The present invention deals with an intelligent device, connected to the internet, for the delivery of medicines to patients automatically and in a controlled manner. In addition, it allows the patient to be checked by measurements of health parameters obtained through external sensors, which are not the object of this invention.

When following a treatment programme, patients use their own methods to take the medicines at the right times, often forgetting to take them, or taking more than one dose by mistake. This generates health complications for the patient and additional costs for health centers or relatives who must deal with the consequences of these situations.

In many cases, people who are in charge of an older adult who is undergoing treatment, do not have a patient monitoring system, which is needed to know if they are following the treatment correctly or in case of detection of an anomaly in the schedules, to advise the patient/user/responsible person to correct the behavior.

In addition, not all patients users/responsible persons are advised on what is the best time to take the doses of prescribed drugs in order to obtain the best results, or which medicines cannot be administered together, when the combination can cause a health problem or the loss of treatment efficacy either due to pharmaco-kinetic, pharmaco-dynamic and/or psycho-chemical interactions between them.

While there are other devices that fulfill some of the functions of the present invention, there are none that include all of them. In the case of the present invention, the novelty is not only the integration of all these functions, but the inclusion of other novel functions.

The devices that are currently available provide interfaces for patients/users that are overwhelming, comprising many buttons, displays, indications, etc., which leads to rejection by the patient/user/responsible person. Additionally, they do not assist the responsible person/user in the loading of the medicines when they are part of a complex treatment.

Thus, the following patents: US2012316405, WO2016141102, US2006124655, U.S. Pat. No. 7,269,476, WO0217850 deal with systems for dispensing drugs and monitoring the vital signs of patients, using a microprocessor system and communication modules, information screen, keyboard or buttons to control the device and others, but lack some functionalities included in this device, such as those detailed below.

On the other hand, the medical assistance centers, health institutions or pharmaceutical laboratories need anonymous statistical information on drug consumption, times when they are taken, etc. to carry out studies and research on the effect of medications under prescribed treatments. The device of the present invention can collect this information anonymously if the user authorizes it and analyze it via Big Data algorithms to obtain information automatically, without using information that can identify the patient/user, rather only the medications administered. Each person can choose not to provide this anonymous information to the system.

The aforementioned patents contain a series of substantial differences to the present invention, namely:

1.1 Screen, Buttons, Display:

Devices which are currently available have a screen, keyboard or buttons, etc. This leads to rejection on the part of the patients/users/responsible person because they understand that the device itself adds complexity that many times they are not willing to face.

To the contrary, the present invention does not have any button or screen on the device. The smartphone application centralizes all the information and commands to be used by the users or the responsible person (family member, health professionals, or patient if they have the capacity). The user only has to use the device when it emits visual and/or audible indications or when the bracelet vibrates. In this way the complexity of the system is markedly diminished for the user.

1.2 Quantity of Medicines:

Current devices provide large capacity containers for storing drugs of the same type. The present invention has 21 compartments in which at least 6 different drugs can be loaded in each of them, providing the opportunity for the necessary different medicines according to the user's treatment needs.

1.3 Internal Quality Measures:

The devices reported so far do not monitor the internal environment of the device. This determines that the medicines are exposed to variations of temperature and/or humidity, which can adversely affect storage conditions and if that happens they will not be apt for consumption.

To the contrary, the device of the present invention has internal measurements of these parameters and alerts those responsible when the internal environment where the drugs are found is not adequate. The device of the invention can also control the humidity/temperature of the container, which guarantees the stability of the medicines and stops the patient taking medications that after being loaded in the dispenser are subject to conditions that alter their active ingredients.

1.4 Artificial Intelligence and BigData Analysis:

The device of the present invention, unlike those already known, can also combine its features together with the storage of relevant information. By means of analysis of BigData and Artificial Intelligence (AI) on the use of medicines, anonymous information on drug consumption by the overall population can be obtained, so that it is able to generate statistics by region, age, gender, etc., thus providing information for institutions and researchers and enabling adjustments to be made in the dosage and/or therapeutic indications of medicines based on what has been learned.

1.5 Drug Interactions:

The known devices do not provide information about drug interactions, so they do not provide alerts as to when such may occur.

However, the claimed device at the time of loading medicines verifies the treatment against a database prepared by health professionals about adverse reactions and interactions between medicines, medicinal herbs, homeopathic specialties and foods, and alerts the responsible person in case it finds any.

1.6 Security:

The device of the present invention, unlike the existing ones, encrypts user data in all stages, as well as the communications with the servers, using the most robust encryption algorithms available (AES256 and TLS/SSL). In addition, it allows remote security updates to implement improvements in the device automatically, in a secure and transparent way for the user, achieving a rapid response to a possible security emergency.

1.7 Performance Tests:

The devices available in the market do not include as a function, a periodic test of their internal systems to detect a malfunction.

The device claimed herein carries out internal predictive tests, imperceptible by the user, while waiting to deliver the medicines. If one of these tests detects a malfunction of the system, it alerts the person in charge to anticipate a failure and avoid putting the patient at risk, allowing him to look for alternatives so the patient receives the medication.

1.8 Storage of Drugs Outside their Packaging:

Currently available devices store the drugs in open containers, this determines that their integrity cannot be guaranteed.

On the other hand, the device of the present invention allows storage of the different tablets in unit doses allowing daily/weekly/monthly loading of treatments, by the pharmacy, nursing, medical service or the user/responsible person. In addition, at the moment that the medicines are being loaded, it is possible to select an option whether the medicine was already removed from its blister or packaging. With this information entered by the responsible person user, the device is able to alert the user/responsible person if the medication contained in it has expired and therefore should not be administered.

1.9 Another characteristic to highlight is that none of the devices in the state of the art is modular, that is, they do not have the capacity to add additional modules with more functions such as: storage capacity, refrigeration, capacity to dispense medicines by injection, etc. This allows you to add/remove functions depending on the specific needs of each user and improve the cost/benefit ratio of the system, allowing only the necessary features to be used depending on the patient's need.

1.10 None of the aforementioned devices permit identification of the patient/user/responsible person at the time of withdrawal of the medication. This determines that the drugs are only released at the right time but anyone can pick them up. The present device identifies to whom the medicines are delivered, avoiding delivery to a person other than the user. This also ensures that, in hospitals, geriatric institutions or any other type of institution where drugs need to be delivered, the person who withdraws them for administration to patients and at what time is identifiable. Thus, the traceability of medicines can be improved and, in the specific case of controlled or prescription drugs (narcotic drugs and psychotropic drugs), it is particularly relevant to know who withdraws them.

1.11 The system of the present invention has voice recognition capability, for example, the device can recognize requests for help, notify a responsible person and/or health center, answer questions of the patient/user/responsible person (such as for example if they have taken medications or if they have to take any more on that day, etc.), respond to voice commands and perform actions (calls, reminders, etc).

Object of the Invention

The object of the present invention is a system connected to the internet comprising an electromechanical device, intelligent peripheral devices and a method for loading and delivering medicines to patients at the time previously programmed, by means of an application (APP) on a Smartphone or Tablet/web/Computer program, all of them controlled by software.

The system seeks to prevent errors in the intake of medications through data analysis, as well as avoiding mistakes in the administration of medications. Intelligent peripheral devices such as the bracelet help to clearly communicate to the patient when taking medication, and allows, among other functions, notification to the responsible person by means of an emergency button located on said bracelet and two-way audio communication between the patient and the user/responsible person.

The system also allows the integration of other intelligent peripheral devices (not the subject of this patent), such as sensors that measure blood glucose, heart rate, blood pressure, body temperature, blood oxygen, or any other health sensor or device available in the market capable of communicating via Bluetooth, wifi or other wireless protocol. These sensors perform approximation analysis and allow both the responsible persons and health centers to collect patient health information. Any intelligent electronic device that has communication capability through some wireless protocol (cell phones, tablet, smart watch, etc.) can also be used as a peripheral device to interact with the system's functionalities.

DETAILED DESCRIPTION OF THE INVENTION

Figure 1:
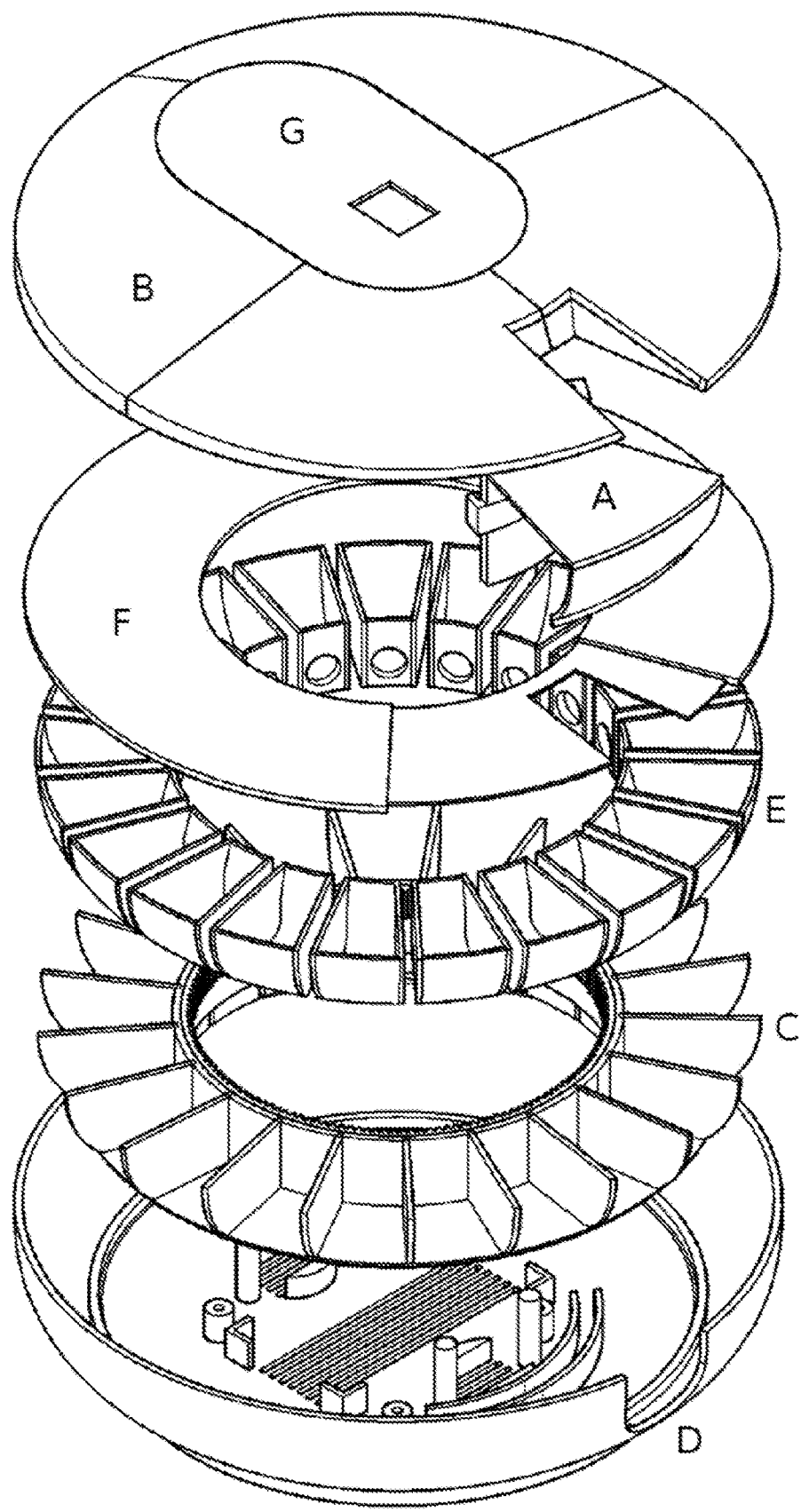
FIG. 1 shows a blown up diagram of the device, where its internal components and assembly can be seen.

The device of the present invention has a mobile gate (A) driven by a motor (not shown), which allows access to medications when the system notifies the patient. At any moment the gate (A) is mechanically closed and it is only possible for the responsible person to open it by using the application or when the system notifies the patient at the appropriate time that the medication should be taken. To do this, the gate (A) has optical sensors for open and closed gate detection and an optical sensor for detection of container vessels.

An upper cover (B) together with a lower cover (D) close the interior of the device and prevent access to medications. It is only possible to access them when the mobile gate (A) is opened, forcing the patient to keep to the schedules established by the system or to the decision of the responsible person in a case of releasing emergency medications. The upper cover (B) has an opening in which the upper plastic cover (G) is placed, leaving the device closed and preventing access to its interior.

The upper cover (B) has a microphone (not shown) to allow two-way communication between the responsible person/user and the patient, together with a speaker (not shown) located in the lower cover (D), also used to emit sounds that make the patient notice that it is time to take the medication.

The inner disc (C) contains compartments to hold the container vessels (E) in which the medications that will be delivered to the user are stored. These compartments have magnets that act as guides to facilitate the placement of container vessels (E).

In an embodiment, the inner disk (C) has 8 compartments, which makes it a portable device, useful for patients who need to transport the drugs.

In another embodiment, the inner disk (C) has 21 compartments. This device is useful for those patients that require 3 daily doses of medication.

In both cases, the capacity of the device allows a weekly load.

Additionally, the inner disk (C) has sensors (not shown), slots (I) and (H) for positioning thereof and a motorized drive (not shown) to place the plate in the desired position according to the programming of the drug that must be delivered In each partition of the inner disk (C) there is a container vessel (E) that allows the user to easily remove the drugs from the device. In addition, each container vessel (E) has a magnet that guides the user/responsible person when inserting the glass into the device. This is of great help to people with motor disorders, since the container vessel as well as the spaces have been designed to simplify extraction by people with these problems.

The lower cover (D) closes the device completely and contains the necessary electronics, motors (not shown) to move the inner disk (C) as well as the gate (A) and the backup battery (not shown), in addition to the electronics necessary (not shown) to control the device.

The upper cover (G) has an RFID reader chip and/or other proximity sensors such as NFC tags, which allow the patient/user to be identified and only deliver the medicines to the correct person. In addition, it has a fingerprint reader which can be used to identify patients/users/responsible persons. It is also possible to detect the proximity of the wristband (or any device with Bluetooth connection (BT)) using the power of the Bluetooth signal, Wifi or Radio Frequency, transmitted by it and its unique address (MAC) to open the gate (A) when the bracelet (ii) is near the device (i).

The upper cover (G) can be replaced by different modules (not shown) which add more functionalities to the device such as refrigeration, more compartments, etc. The upper plastic cover (G) contains LED lights (not shown) that allow visual indications to the patient to make him notice that he must use the device to take the medicines.

The lid (F) fulfills the role of making an upper lid for the container vessels (E) and also functions as a limit to the lateral movement of the gate (A).

All the components of the device described here can be made of different materials depending on the use that is given to it, such as polymers, aluminum, wood, steel, etc.

Figure 2:
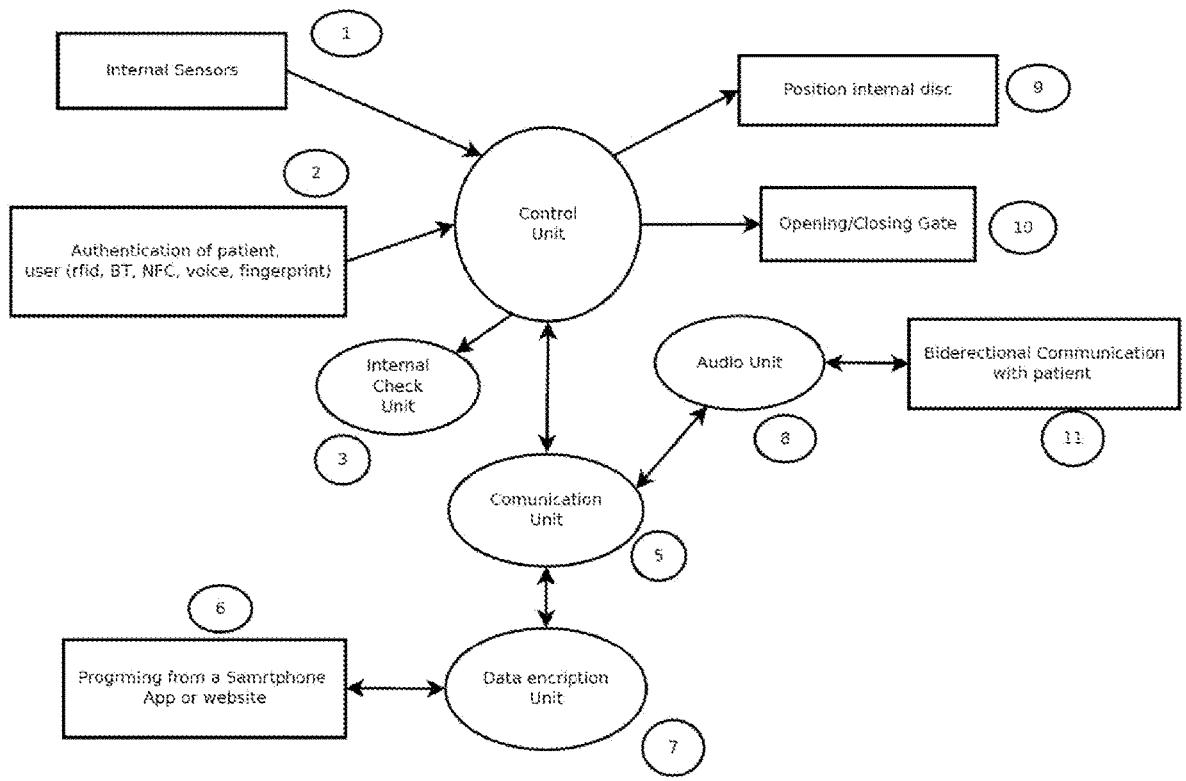
FIG. 2 shows a block diagram that reveals the interaction between the sensors and activating components, as well as the software that controls the device and that is carried out in the control unit.

According to FIG. 2, the device contains the control and communication electronics with a microprocessor, memory and wireless communication modules. More specifically, internal sensors (1) provide information to the Control Unit (4) which has a microprocessor (not shown). The sensors (1) provide positioning information on the inner disk (C), the opening and closing of the mobile gate (A) and the open device covers (B and D). The position measurements are used to position the disk (C) at a time to take medication (see internal disc positioning system) and to verify if the device has been opened in an unusual way. All these generate notices to the responsible person in case of an unusual situation or warning.

The patient/user/responsible person authentication module (2) contains integrated circuits for reading user and/or patient information such as an RFID tag which is used to identify the same and only allow that person to withdraw the medication. In addition, it is possible to use the identification of Bluetooth peripherals (MAC address) to identify the patient/user/responsible person by measuring the power emitted from the Bluetooth signal of the wristband. The device may alternatively have a fingerprint reader or other electronic means of biometric or other identification to allow the user to withdraw the medication.

The authentication module of the patient/user/responsible party (2) also allows identification of any user of the system, such as those responsible for the patient and other possible users such as nurses, doctors, etc. so that any user of the system can use the identification modules, as these modules fulfil different functions depending on the case. For example, a nurse can be notified through these modules that it is time to collect medications from the device to deliver to a patient.

The internal check unit of the device (3) is responsible for conducting periodic internal tests and collecting information on the operation of the device to anticipate possible failures thereof and immediately notify the responsible person or health service. The tests consist of making small movements of both the main disk (C) and the mobile gate (A), measuring the current consumption of the motors (not shown) while the movement is made. This allows for comparison of the consumption values against the standard values and warning of a deviation, which would indicate that the device is operating incorrectly, for example, with some obstruction in movement, which would increase the current of the motors. The device also has sensors to measure the temperature and internal humidity of the compartment to know if the medicines inside are in correct conditions and alerting if any limit has been exceeded. As part of the internal tests, the status of the internal battery is also checked to warn of possible deterioration.

The control unit (4) is equipped with a microprocessor that receives information from all the sensors (1) of the device, as well as commands through the communications unit (5) and performs the electromechanical control of the device, movement of the inner disk (C) and gate (A), validation of authorized persons and registration of the time for delivery of medicines. The unit contains software that performs all the described functions of the device and allows it to be updated remotely in the following way: The device periodically consults the backend servers (iv) to see if there is a new command for the device according to its address logic. If the command is "update firmware", the device downloads the new program from an authorized server, copies it to its internal memory and proceeds to execute it, thus continuing to work with a newer version. During the download of the new program, the authenticity of the server is verified through an SSL certificate, thus only allowing a new program to be downloaded from the authorized servers.

The communications unit (5) handles communications with the "backend" servers (iv) that manage the information and commands given to the device (i). It uses an integrated communication module (see Modes of communication), connected to the Wi-Fi, 3G or LTE network or similar system of the user to access the servers (iv) from where it receives commands and exchanges information for the operation of the device (i). At the same time, it handles communication via Bluetooth (BLE) with other peripheral devices of the ecosystem, such as the alert/measurement bracelet and other sensors that allow for information about the patients health to be obtained.

The device (i) allows programming by means of software that can be executed on any platform such as a smartphone operating system or a web application (6). In this way users program the dosage of their medications, create treatments and allow it to see all the historical information stored.

To program the treatments, information such as the start and end date thereof, the medications and doses required, and the times between ingestion are inputted. This information will then be used by the system to calculate the timing of the intakes and to verify that there is no interaction between the medications used for this or other treatments of the patient. This information, after removing the personal patient information, will be used to obtain anonymous statistics on the use of medications, for what treatments they are used and the times at which they are taken, among other possibilities.

The data encryption unit (7) allows all communications to and from the device to be encrypted with TLS SSL/AES256. Therefore, the system has hardware capable of performing the data encryption and decryption operations in real time. This includes communications related to commands given to the device (i), as well as any information exchanged with the servers (iv) and two-way audio communication (8).

The audio unit (8) and the two-way communication unit with the patient (11) allow two-way audio communication between the patient and the person in charge or health center, in real time and via the Internet, in an encrypted form. A speaker and microphone mounted on the device, as well as on the wristband, are used to perform this function.

The positioning system of the internal disk (C) uses the information from an optical sensor (not shown) by which, and via the slots (not shown) of the inner disk, the position of the disk (C) is controlled according to the movements made. The disk (C) has a special slot that is one size larger (H) than the slots of the rest of the positions (I), which allows detection of the zero position of the disk (C) and from there keeps track of the other positions until returning to the zero position. The disc (C), depending on the current position and the desired position, is moved clockwise or anti-clockwise by a step motor (not shown), which is used until the desired position is reached.

The drive for opening and closing the mobile gate (A) has a step motor (not shown) capable of moving the gate (A) to allow the patient/user access to the medicines. It also has an open gate sensor and a closed gate sensor (not shown), to verify its total opening and closing. This is due to the necessity of verifying the correct positioning of the gate, since the delivery of the medication to the patient depends on it. Unlike other existing devices, the advantage of the present system is that it has a single gate for administering medicines, allowing a robust and fail-safe construction, as well as the inclusion of the necessary sensors to detect its correct functioning. In addition, the way in which it is configured allows the container vessels to be removed more quickly and easily.

Figure 3:
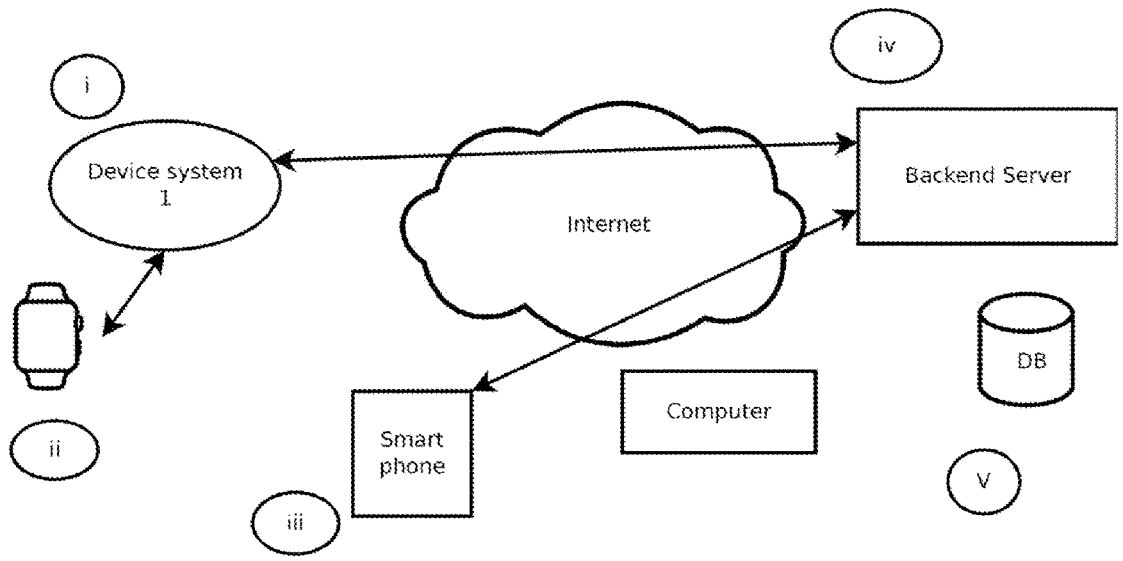
FIG. 3 shows a diagram of how different parts of the system communicate through the Internet, including back-end servers and other devices associated with the ecosystem.

Modes of communication: as shown in FIG. 3 the device of the present invention (i) communicates through the protocols Wifi 802.11 b/g/n/e/i using a frequency of 2.4 GHz fully compatible with home and professional devices, additionally protected with the TLS SSL security protocol. The device (i) communicates through the Internet with the back-end servers (iv) which contain the necessary software to communicate in turn with the smartphone of the responsible person/user or administration software of the health center (iii).

The servers also make use of a database (for example, SQL) (v) that stores information about the interaction between the medicines, the treatments loaded by the users, the times and medicines that the users take, amongst others. The smartphone of the responsible person (iii), or the administration software used (iii) by the health centers, communicates in an encrypted manner with the backend servers, guaranteeing a secure transfer of information between the system components. Also, the servers act as an intermediary to re-transmit the commands given by the responsible person's/user's application (iii) to the managed devices.

The device (i) of the present invention communicates with one or more peripheral devices (ii) by means of Bluetooth Low Energy, Wifi or other wireless protocols. Peripheral devices such as the bracelet (ii) allow the patient/user to be alerted when it is time to take a medication. The device (i) sends to the wristband registered for the patient/user, the days and hours at which the medication must be taken. In this way constant communication between the wristband (ii) and the device (i) is not necessary, saving energy and consequently battery usage.

The bracelet (ii) contains a program that constantly checks the alarm time against the current time, and activates the vibration and visual and audible indications to let the patient/user know that he/she should use the device to remove the medication. In addition, the bracelets (ii) are used to check the patient/user, using the power emitted by the Bluetooth signal and the MAC address thereof, which is unique. The bracelet (ii) permits measurement of health parameters such as heart rate and blood pressure, which can then be seen from the smartphone application or web interface at the health center.

It is possible to connect other peripheral devices (ii) to the device (i) such as meters of different health parameters and allow the responsible persons or health centers to access the information they provide.

The software (iii) that runs on the smartphone of the responsible person permits registration of treatments indicated by the doctor, using the name of the medication, the number of hours between each intake, the start and end dates of the treatment, the attending physician and a comment field. After creating one or several treatments, the person in charge can choose to load the device selecting one of the previously loaded treatments. The loading of the treatments is done by the user/responsible person assisted by the application.

In manual loading the responsible person can choose to load each medication, or insert a container (E) preloaded into the device (i) that can be carried out by a pharmacy or health center. The loading of the medications is done by the user/responsible person assisted by the application. During loading, medications are entered through the mobile gate (A) as explained in the Drug Loading section.

Figure 4:
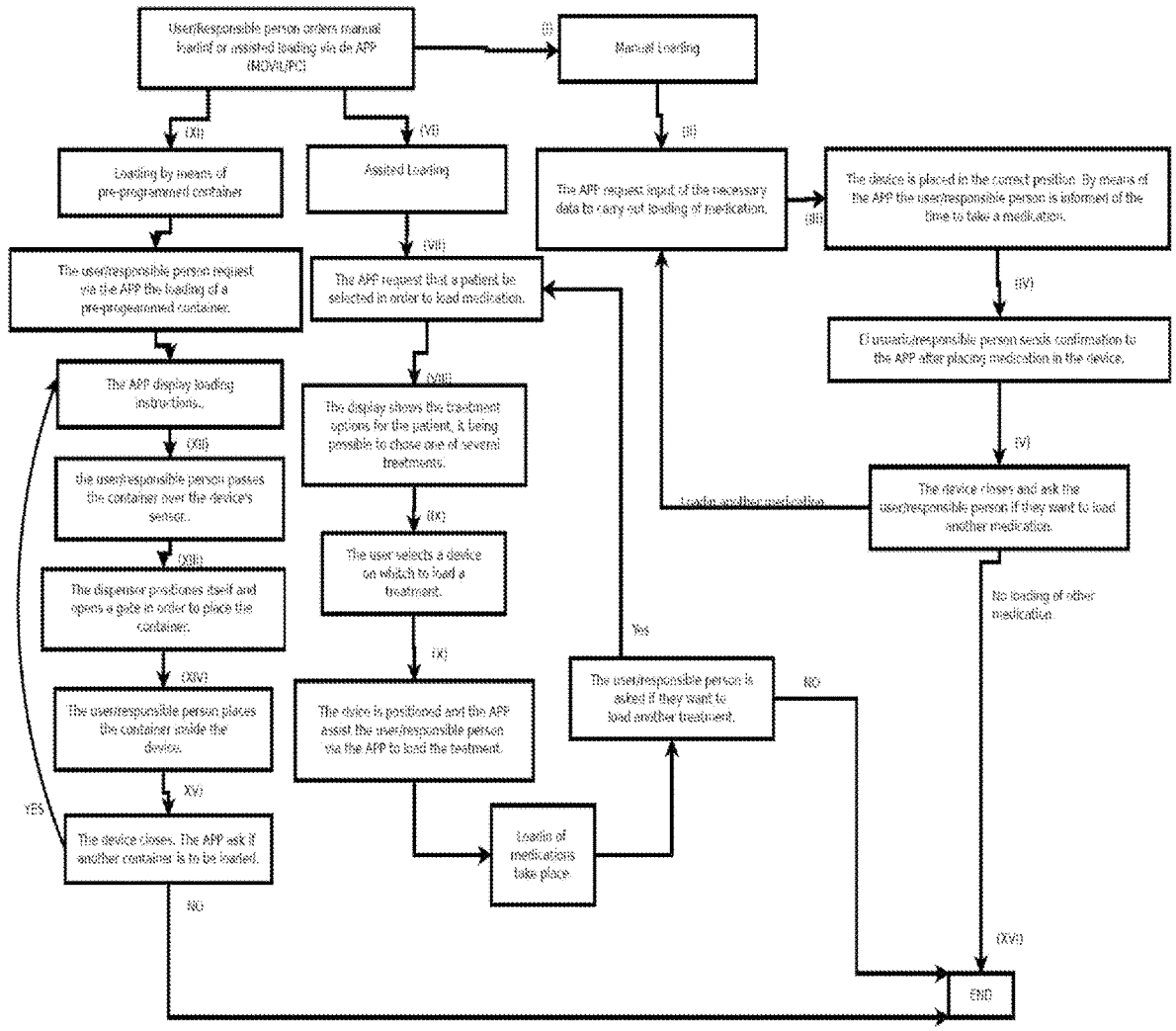
FIG. 4 is a flowchart for the different types of loads that the device contains.

Functioning:

Method for Loading Medications:

As shown in FIG. 4, the user has three options for loading the medications in the device: "manual loading", "assisted loading" or "loading with pre-programmed container".

Manual Loading:

After selecting the manual load (I), the APP requests entry of the necessary data to carry out both the loading of information and the physical loading of the medication (II). Then the pillbox is placed in a free compartment and it tells the user the steps necessary to load the medications (III). At the end of the placing of the medication, the device detects the load and asks the user if it is correct that he has placed the medications in the device (IV). In the event that the user carries out the loading, the manual loading procedure ends, otherwise it starts again with the manual loading procedure (V). All the steps are guided by the system via the APP.

Assisted Loading:

In order for the user to select the assisted loading (VI), he must have previously entered a treatment (see Loading of Treatments). Once the user selects the assisted loading, the system asks to choose a patient for whom they want to load a treatment. After selecting the patient (VII), the system presents a series of treatments to be loaded (VIII) on the screen, of which one or more can be selected to be loaded on the device.

This loading contains information on the name of the medication, after how many hours it should be taken, the dose required, the start and end date of the treatment and the doctor in charge if applicable.

When selecting treatments, the user must choose on which device he wants to load the treatment (IX). When the device has been chosen, it is positioned with a free compartment and guides (X) the user/responsible person in order to load the treatments using the APP. At the end it asks the user if he wants to load another treatment. If "no" is selected, the loading is finished, otherwise the assisted load starts again from the beginning.

All the steps are guided by the system via the APP; in this way, the system suggests the best schedules trying to avoid interaction between the drugs, according to the technical information stored in a system database. It is also possible for the user to schedule the delivery times of medications manually.

Loading Per Container:

In the customized container vessel loading mode, the controller simply brings the closed container vessel (E) to the device (i) and recognizes it thanks to an RFID, ST or any other radio frequency reader (not shown), obtaining the data of its contents, as well as date and time, correlating it to the treatment previously entered by a pharmacy, health center or responsible person. This prevents the user from entering all the information again, making the loading of medicines faster. The personalized container vessel (E) also helps the medicines maintain their storage conditions and ensures that the patient ingests them together.

When selecting the load per preprogrammed container (XI), the system displays the loading instructions in the APP. Then the user brings the vessel close to the RFID sensor or another on the pillbox (XII). The pillbox detects and processes the code of the container and after consulting the servers opens the gate for the user to place the preprogrammed container (XIII) in the device. When placing the vessel (XIV), the system asks the user if he wants to carry out another loading of the preprogrammed container (XV). If "no" is selected, the loading is finished (XVI). Otherwise, the loading of the preprogrammed container starts from the beginning (XII).

Control of Medicinal Interactions:

The interaction check consists of verifying the medicines that are being administered to the patient against a database prepared by health professionals (v), whatever their mode of loading. Upon detecting that the loaded medications interact in some way, a warning is issued to the responsible person to review them together with the medical body involved.

Figure 5:
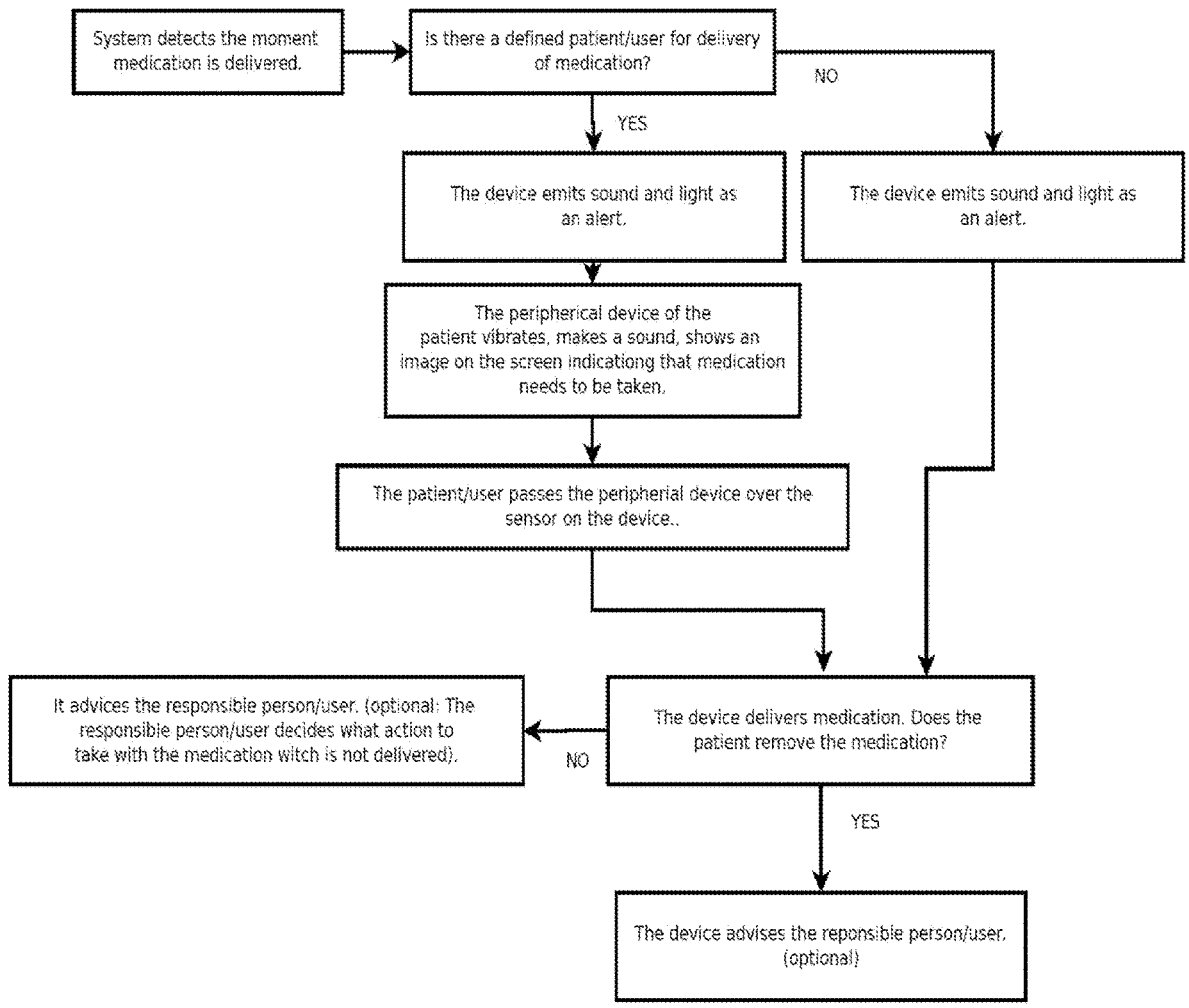
FIG. 5 is a flowchart showing how the system delivers the drugs already loaded and programmed for a specific time and day.

Method of Delivery of Medicines:

Medicines Programmed for a Specific Date and Time:

FIG. 5 details the procedure by which the system delivers loaded and scheduled medications for a specific time and day.

When the system detects that drugs must be taken, the system checks whether said medications have an assigned patient/user. In the case of having an assigned patient/user, the pillbox, by means of lights and sounds, generates announcements for the patient/user to withdraw the medication. In case of there being no patient/assigned user, any person can withdraw the medication from the device without having to provide authentication.

If the medications have a patient/assigned user, in addition to alerting by means of lights and sounds from the pillbox, the system generates warnings by means of vibration, sound, visual indications, etc. in the peripheral device assigned to the patient/user.

To withdraw the medications, the patient/user must bring their peripheral device (ii) (a bracelet or similar device) towards the pillbox which will identify it and open the gate (A) to remove the medication. In this way only the correct patient/user can access the medication.

In the event that the medication is not withdrawn, the system generates a warning to the responsible person to take the pertinent action.

In all cases if the medicines are not collected in time, the person in charge can decide whether to release them or not remotely from the smartphone APP. In any case, it is possible to configure the number of retries to permit delivery of the medication, changing the number of repetitions and the waiting time between warnings. All system warnings are configurable for both the patient/user and the responsible party.

Figure 6:
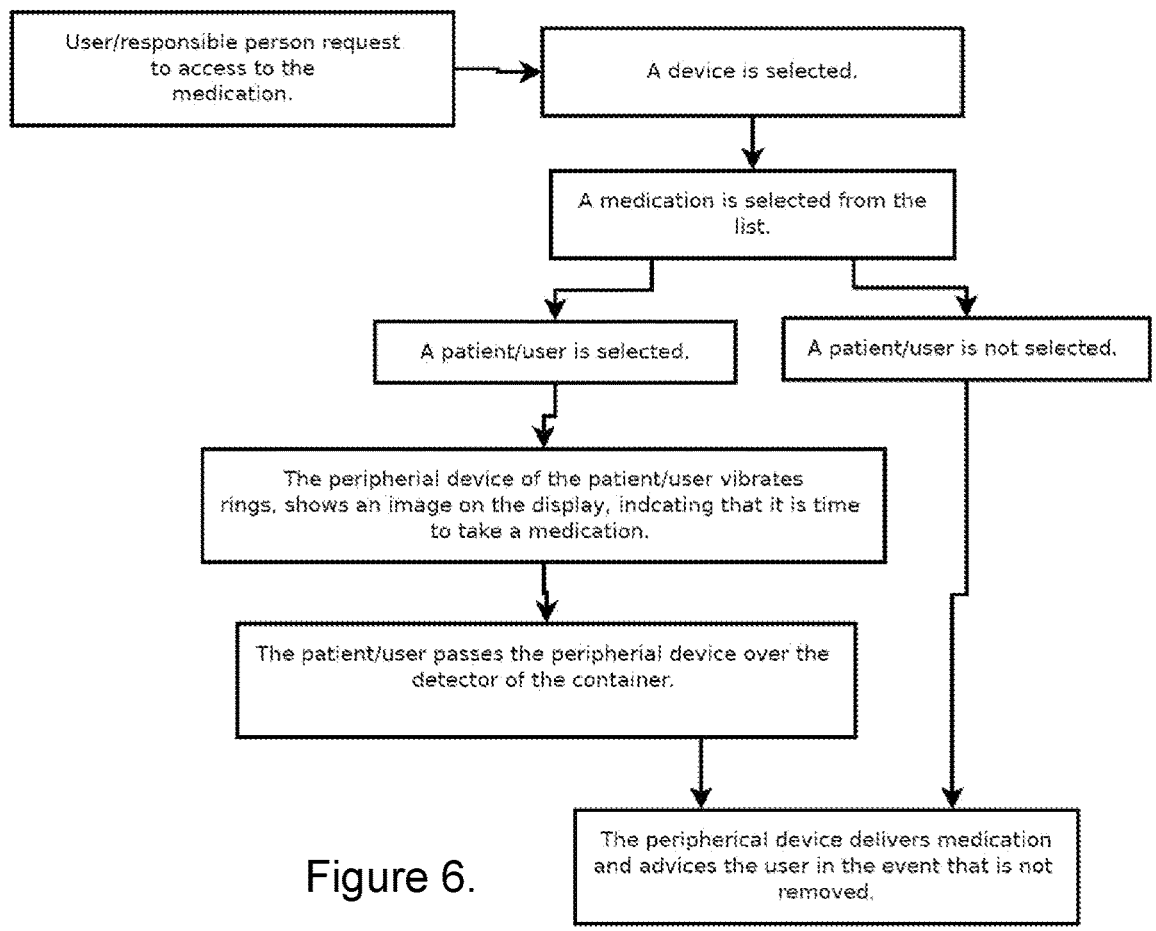
FIG. 6 describes the procedure by which the system delivers the medication that must be delivered in an emergency to a patient.
Figure 7:
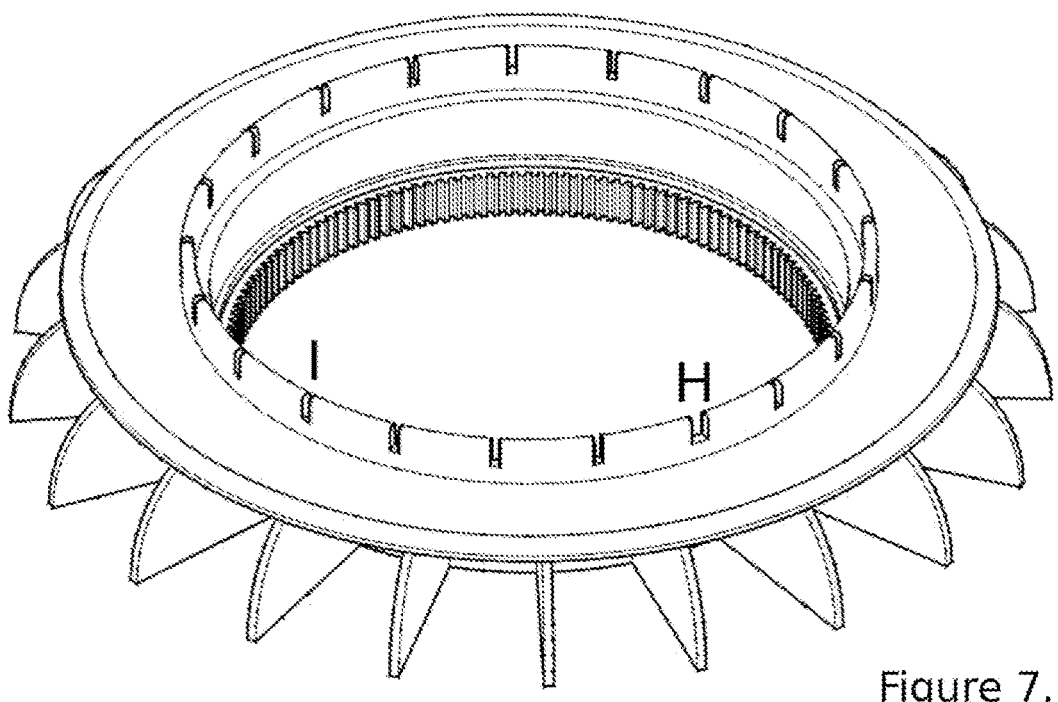
FIG. 7 shows a detail of the inner disk (C) identifying the slots of the same size (I) and the single slot of a different size (H).

Delivery of Medicines in Emergencies:

FIG. 6 describes the procedure by which the system delivers to a patient/user medications that were previously identified for emergency delivery. The user/responsible person requests via the APP release of an emergency medication. The user selects a pill dispenser that he/she has permission to manage and the system displays all the medicines present in it for a manual delivery. The user/responsible person selects the medication that he wishes to deliver from the list and a patient to pick up the medication. In the case that no particular patient/user is selected, the pillbox, by means of lights and sounds, generates announcements for the patient/user to withdraw the medication without requesting any identification. In the event that the medication is not withdrawn, a warning is generated to the person responsible to take the pertinent action. If the user/responsible person assigns a patient when requesting emergency delivery, in addition to alerting by means of lights and sounds in the pillbox, the system generates warnings by means of vibration, sound, visual indications, etc. in the peripheral device (ii) assigned to the patient/user. To withdraw the medication the patient/user must bring their peripheral device towards the pillbox which will identify them and open the gate so that only the patient/assigned user can withdraw this medication. In this way only that patient/user can access the medication. In the event that the medication is not withdrawn, the system generates a warning to the person responsible to take the pertinent action. In all cases if the medicines are not collected in a timely manner, the responsible party can decide whether to release them or not. It is also possible to configure the number of retries to deliver the medication, entering the number of repetitions allowed and the waiting time between notifications. All notices from the system are configurable for the patient, user or responsible person.

Warnings Given by the System:

Warnings to Take Medicines:

When the scheduled time to take a medication arrives, the device (i) turns on its LED indicators (not shown) to make the patient/user notice that he/she should approach it to withdraw the medications. It also emits sounds and vibration to the bracelet (ii) if it is configured for this.

When the patient/user approaches with his bracelet (ii), the device recognizes it and opens the gate (A) so that he can extract the medication. This gate (A) only opens upon recognition of the bracelet (ii), biometric parameters/voice or by command of the responsible person by using the Smartphone or Web application. If the user does not approach the device to take the medication for a pre-configured amount of time, a notification is issued to the responsible person, either to his Smartphone or another application, to make him notice the deviation in the treatment. The person in charge can then contact the patient/user using integrated two-way audio communication to request the medication, Warning of Unauthorised Opening of Device:

When the top cover of the device is opened, if it was not done following the normal opening protocol by request from the application, the device issues an alert to the responsible person's application notifying them. This can avoid situations in which someone wants to alter the interior of the device, or access all medications at the same time.

Emergency Warnings from Bracelet:

The bracelet (ii) has an emergency button that the patient can press so that the responsible person/user or health center receives an emergency notification. The next thing that should be done after receiving a notification of this type is that the person in charge will communicate with the patient using integrated two-way audio communication to know what has happened and to be able to assist him/her.

Warning of Internal Defect:

The system performs internal functional tests periodically (see Internal Function Test). If it detects an operational problem, it will issue a notification to the responsible person or assistance center, thereby anticipating any possible failure. Once the notice has been received from the responsible person or health center, the person in charge should contact the patient through the two-way audio communication to resolve the problem or take palliative actions to ensure that the patient receives the medication, Release of Medication on Demand:

The user/responsible person, through the application of a Smartphone or web interface, can request the release of medicines remotely at any time that the device (i) is connected to the internet. For this, the medications must have been defined and loaded in any of the disk (C) compartments of the device and defined by means of the APP as a delivery compartment on demand. This covers emergency situations in which the patient/user is required to pick up a specific medication, but does not want to leave it to the patient to decide freely. In addition, it is recommended that emergency medications for children with chronic diseases are controlled, to ensure that they receive the medications when the adults in charge consider it necessary. Also, this function can be used as an emergency kit allowing controlled access to medications.

Measurement of Pulse/Pressure or Other Health Parameters Using Peripheral Devices:

The responsible person, through the software, such as a smartphone user or web interface (iii), can request that peripheral devices of the patient (ii) perform a measurement of heart rate, pressure or other physical tests supported by the peripheral device, remotely, obtaining the result in seconds. These health measurements are an approximation analysis that can be used by health centers or responsible persons to estimate the patient's condition remotely.

Measurement of Movement from Accelerometer Bracelet:

The responsible person, through the use of a smartphone or web interface (iii), can request the bracelet (accelerometer) provide historical information saved on the device. In an emergency situation or inability to contact the patient by other means, this functionality of the bracelet allows the responsible person or the health center to know if the patient has vital signs (movement, heart rate, etc.)

Means of Use:

Domiciliary: The described device can be used in a home environment, where the responsible person can be a relative of the patient and administer the loading of the medications in the device, or it can be the patient themselves, if they are sufficiently lucid to carry out the tasks. In this modality, the device has 21 compartments, which may contain medications for different family members, and/or emergency medications to be released by the responsible person when deemed appropriate. In this mode the device is also useful to control the taking of medicines by the family, especially children, allowing controlled access and historical information on the consumptions of each member. The device enables different modules to be placed by removing the upper plastic cover (G). For example, a refrigerant module (not shown) which allows control of temperature and humidity of the drugs inside the device. This functionality is very useful in climate zones where the ambient temperature compromises the stability of the medicines.

Portable: The portable device contains less distribution units and is designed to be lightweight and smaller (for example for 5 to 7 deliveries), allowing patients/users to take the medicines in the aforementioned pillbox and remind them when it is necessary to take the medicines. It's use is also recommended for children who must be medicated, and allows for release of medicines in an emergency by the responsible person.

Refrigerated laptop: The portable refrigerated device is similar to the portable one, but it contains less distribution units for storing medicines and it works with a temperature control system in order to guarantee the storage of the medicines in suitable conditions. It is specially designed for critical medicines that need to be stored in a refrigerated environment or used in climate zones with high temperatures. In this mode, the device registers the temperature periodically so that the person in charge can verify that the medicines are in adequate conditions.

Geriatric institutions: Use in geriatric institutions, where there are older people taking multiple medication is particularly convenient. It is possible for a single user/responsible person (for example, a nurse) to administer the medications in several pillboxes and for several patients, controlling the administration at the time indicated for each patient without effort. In addition, it is possible to generate reports for relatives of patients with statistical information about the delivery of medications. By allowing sensors to be attached to the device (for pressure, glycaemia, cholesterol, etc.) one can have a more accurate control of patients in real time, avoiding human errors.

Hospitals and home internment: The use of the device the object of the invention in hospitals allows one to keep the drugs under control, registering who has made a withdrawal, for what patient it was used and at what time. This information is of vital importance so that hospitals can maintain the traceability of medicines at all times. The same functions as for home hospitalization mode are available as if the patient were in the same location, but it is the person in charge from the hospital who enables delivery of the medicines remotely.

The invention claimed is:

1. A system for the management, safe dispensing of medicines and the control of patient health parameters, comprising:
   an electromechanical device comprising:
   an inner disk having a plurality of same size compartments (C), each having a position-determining slot, wherein one of said position-determining slots has a size larger than a size of the rest of said position-determining slots defining a zero-starting position;
   container vessels (E) configured to be stored on said compartments (C);
   a gate (A) provided to control access to said compartments (C) one at a time and an electric motor configured to move said gate (A) between an open and a close position;
   gate optical sensors for detecting said open and closed positions of the gate (A), a compartment optical sensor for detecting a position of said compartments (C), and a vessel optical sensor for detecting removal of said container vessel (E);
   a lid (F) covering said container vessels (E) and configured to limit lateral movements of the gate (A); and
   an upper cover (B) including a complementing cover (G) and a lower cover (D) defining a housing enclosing the electromechanical device;
   at least one intelligent peripheral device configured to take biometric measurements of a person and for sending alerts; and
   a control unit configured to receive information from a software application on a remote device to control loading and delivery of medicines.

2. The system according to claim 1, wherein said compartments (C) include magnets for aiding in positioning said container vessels (E) within the compartments (C).

3. The system according to claim 1, wherein operation of the electromechanical device is wirelessly controlled by said software application.

4. The system according to claim 1, further comprising an internal environment control module and a wireless communication module provided to receive and consult biometric measurements of a patient, history of medicines and treatments administered to the patient, environmental parameters, and operation of the electromechanical device.

5. The system according to claim 1, wherein the electromechanical device is controlled to voice commands.

6. The system according to claim 1, wherein a manual loading of medicines is performed by:
   a) entering into said software application medicine information per container and placing said medicines into respective container vessels (E);
   b) controlling the electromechanical device to open said gate (A) to provide access to empty compartments (C) so that said container vessels (E) are loaded into respective compartments (C) according to said loading information;
   c) detecting loading of said container vessels (E) and confirming via said software application completion of the manual loading of medicines.

7. The system according to claim 1, wherein an assisted loading of medicines is performed by:
   a) selecting an assisted loading procedure in said software application;
   b) choosing a patient in said software application;
   c) presenting on said software application at least one treatment;
   d) selecting said at least one treatment and indicating medicines to be placed into respective container vessels (E) based on said at least one treatment;
   e) controlling the electromechanical device to open said gate (A) to provide access to empty compartments (C) so that said container vessels (E) are loaded into respective compartments (C) according to said at least one treatment.

8. The system according to claim 7, wherein the electromechanical device to be loaded with medicines is selected on said software application.

9. The system according to claim 1, wherein loading with pre-programmed container vessels is performed by:
   a) selecting a pre-programmed container vessels procedure on said software application;

b) placing at least one pre-programmed container vessel (E) in proximity to said housing to detect on process a code on said at least one pre-programmed container vessel (E);
c) controlling the electromechanical device to open said gate (A) to provide access to empty compartments (C) so that said at least one pre-programmed container vessel (E) is loaded into a respective compartment (C).

10. The system according to claim 1, wherein a scheduled delivery of medicines is performed by:
a) generating notifications at a scheduled time by at least one of the control unit or said at least one intelligent peripheral device;
b) recognizing proximity of said at least one intelligent peripheral device to said housing; and
c) controlling the electromechanical device to open said gate (A) to provide access to said medicines.

11. The system according to claim 10, wherein the medicines are accessed by any person without authentication.

12. The system according to claim 10, wherein access to said medicines is selectively controlled by said software application when said medicines are not retrieved within a period of time; a number of retries allowed to deliver the medicines, a number of repetitions and a waiting time between notifications is modified with said software application.

13. The system according to claim 10, wherein proximity of said at least one intelligent peripheral device to said housing is done by at least one of biometric parameters or voice recognition.

14. The system according to claim 10, wherein a warning notification is generated when said medicines are not withdrawn from said compartments.

15. The system according to claim 1, wherein an emergency delivery of medicines is performed by:
a) requesting emergency delivery of medicines on said software application;
b) selecting on said software application medicines to be delivered and a pickup person; and
c) notifying the emergency delivery of medicines on said at least one intelligent peripheral device of the pickup person.

* * * * *